(12) United States Patent
Satsuka et al.

(10) Patent No.: US 9,579,086 B2
(45) Date of Patent: Feb. 28, 2017

(54) ULTRASONIC DIAGNOSTIC APPARATUS AND METHOD OF CONTROLLING ULTRASONIC DIAGNOSTIC APPARATUS

(71) Applicant: Konica Minolta, Inc., Tokyo (JP)

(72) Inventors: Tomohiko Satsuka, Tokyo (JP); Yosuke Kimura, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 240 days.

(21) Appl. No.: 14/256,484

(22) Filed: Apr. 18, 2014

(65) Prior Publication Data

US 2014/0323870 A1     Oct. 30, 2014

(30) Foreign Application Priority Data

Apr. 26, 2013   (JP) ................................ 2013-093452

(51) Int. Cl.
    *A61B 8/14*     (2006.01)
    *A61B 8/00*     (2006.01)

(52) U.S. Cl.
    CPC ................ *A61B 8/56* (2013.01); *A61B 8/465* (2013.01); *A61B 8/467* (2013.01); *A61B 8/54* (2013.01); *A61B 8/461* (2013.01)

(58) Field of Classification Search
    CPC ......... A61B 8/461; A61B 8/465; A61B 8/467; A61B 8/54; A61B 8/56
    See application file for complete search history.

(56) References Cited

U.S. PATENT DOCUMENTS

2008/0146922 A1*  6/2008  Steins ................... A61B 8/546
                                              600/437

FOREIGN PATENT DOCUMENTS

| JP | 05-261096 | 10/1993 |
| JP | H1137545 A | 5/1999 |
| JP | 2005323845 A | 11/2005 |
| JP | 2010244202 A | 10/2010 |

OTHER PUBLICATIONS

Notice of Reasons for Rejection dated Sep. 13, 2016 from corresponding Japanese Application; Japanese Patent Application No. 2013-093452; English translation of Notice of Reasons for Rejection; Total of 7 pages.

* cited by examiner

*Primary Examiner* — Mark Remaly
(74) *Attorney, Agent, or Firm* — Lucas & Mercanti, LLP (57) ABSTRACT

The present invention is intended to reduce the consumption of a battery while appropriately performing operation in the case where an AC power source is disconnected and power supply is switched to the battery. An ultrasonic diagnostic apparatus including: an AC adapter connection detecting section (13) that detects whether the ultrasonic diagnostic apparatus is electrically connected with the AC power source; and a display section (10), wherein, when the AC adapter connection detecting section (13) detects that the AC power source is disconnected, power supply is switched to power supply from the battery (11), and an operation screen for controlling an amount of the power supply in the ultrasonic diagnostic apparatus is displayed on the display section (10).

12 Claims, 10 Drawing Sheets

ULTRASONIC DIAGNOSTIC APPARATUS AND METHOD OF CONTROLLING ULTRASONIC DIAGNOSTIC APPARATUS

CROSS REFERENCE TO RELATED APPLICATIONS

This application is entitled and claims the benefit of Japanese Patent Application No. 2013-093452, filed on Apr. 26, 2013, the disclosure of which including the specification, drawings and abstract is incorporated herein by reference in its entirety.

TECHNICAL FIELD

The present invention relates to an ultrasonic diagnostic apparatus for use in the medical field which can be connected to a power source, and a method of controlling the ultrasonic diagnostic apparatus.

BACKGROUND ART

Conventionally, ultrasonic diagnostic apparatuses have been used which operate with power supplied from a commercial AC power source. In recent years, however, ultrasonic diagnostic apparatuses which allow switching between a commercial AC power source and a rechargeable battery have been used in order to deal with various use modes of ultrasonic diagnostic apparatuses. PTL 1, for example, discloses a configuration in which a power source unit having a rechargeable battery is connected to an ultrasonic diagnostic apparatus, and this power source unit can switch between an AC power source and the battery. Specifically, in this configuration, when an input from the AC power source is detected, the power from the AC power source is supplied to the ultrasonic diagnostic apparatus, and when no input is detected from the AC power source, the power from the battery is supplied to the ultrasonic diagnostic apparatus.

CITATION LIST

Patent Literature

PTL 1: Japanese Patent Application Laid-Open No. 5-261096

SUMMARY OF INVENTION

Technical Problem

However, there is a problem that, when power is supplied from a battery, the period during which power is supplied to the ultrasonic diagnostic apparatus is short due to the limitation on the chargeable amount of the battery.

Examples of the case where a commercial AC power source is disconnected to switch to a battery include the case where the user wants to move the ultrasonic diagnostic apparatus without completely turning off the power so as not to change the setting, in other words, the ultrasonic diagnosis is not performed, and the case where ultrasonic diagnosis is performed while receiving power from the battery. In the ultrasonic diagnostic apparatus, the component to which power has to be supplied and the amount of the power to be supplied differ depending on whether ultrasonic diagnosis is performed or not.

Solution to Problem

To achieve an intended purpose, in an ultrasonic diagnostic apparatus according to an embodiment of the present invention that allows an ultrasonic probe, an AC power source and a battery to be connected to the ultrasonic diagnostic apparatus, the battery being a rechargeable power source, the ultrasonic diagnostic apparatus includes: a transmission control section that controls generation of a transmitted electric signal for transmitting ultrasonic waves from the ultrasonic probe to a subject; an ultrasonic reception section that acquires a received signal based on reflected ultrasonic waves received by the ultrasonic probe; an AC adapter connection detecting section that detects whether the ultrasonic diagnostic apparatus is electrically connected with the AC power source; and a display section, wherein, when the AC adapter connection detecting section detects that the AC power source is disconnected, power supply is switched to power supply from the battery, and an operation screen for controlling an amount of the power supply in the ultrasonic diagnostic apparatus is displayed on the display section.

To achieve an intended purpose, in a method of controlling an ultrasonic diagnostic apparatus according to an embodiment of the present invention that allows an ultrasonic probe, an AC power source and a battery to be connected to the ultrasonic diagnostic apparatus, the battery being a rechargeable power source, the method includes: controlling generation of a transmitted electric signal for transmitting ultrasonic waves from the ultrasonic probe to a subject; acquiring a received signal based on reflected ultrasonic waves received by the ultrasonic probe; and, when electrical disconnection of the AC power source is detected, switching power supply to power supply from the battery while displaying on the display section an operation screen for controlling an amount of the power supply in the ultrasonic diagnostic apparatus.

Advantageous Effects of Invention

According to the present invention, when it is detected that the connection between the AC power source and the ultrasonic diagnostic apparatus is cut off, the power supply is switched to the power supply from the battery and the display section displays the operation screen for controlling the amount of power supply in the ultrasonic diagnostic apparatus, and thus the user can operate the operation screen to control the amount of the power supply in the ultrasonic diagnostic apparatus. Consequently, when the power supply is switched to the power supply from the battery, the operation can be appropriately performed, while reducing the consumption of the battery power.

DESCRIPTION OF EMBODIMENTS

In the following, an embodiment of the present invention will be described in detail with reference to the accompanying drawings.

Embodiment 1

Figure 1:
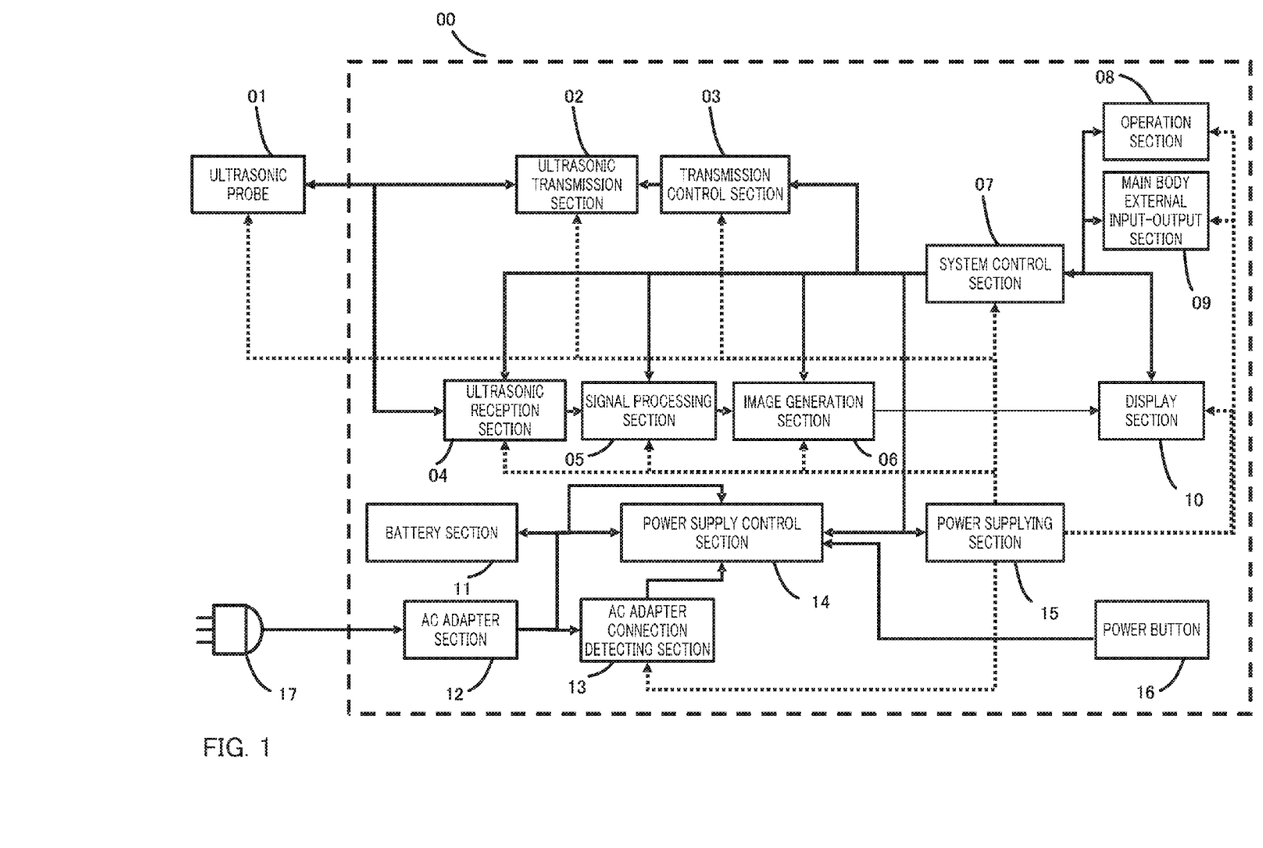
FIG. 1 illustrates a configuration of an ultrasonic diagnostic apparatus according to Embodiment 1 of the present invention.

FIG. 1 is a block diagram illustrating a configuration of an ultrasonic diagnostic apparatus according to Embodiment 1 of the present invention. Ultrasonic diagnostic apparatus main body 00 of the present embodiment includes ultrasonic transmission section 02, transmission control section 03, ultrasonic reception section 04, signal processing section 05, image generation section 06, system control section 07, operation section 08, main body external input-output section 09, display section 10, battery section 11, AC adapter section 12, AC adapter connection detecting section 13, power source control section 14, power supplying section 15, and power button 16. The ultrasonic diagnostic apparatus main body 00 can be connected to ultrasonic probe 01 and power plug 17.

To ultrasonic diagnostic apparatus main body 00, power is supplied through battery section 11 or power plug 17 from an external AC power source.

Ultrasonic diagnostic apparatus main body 00 is activated when power button 16 is pressed down, and power source control section 14 performs a control such that power is supplied from power supplying section 15 to each component.

Under the control of power source control section 14, power supplying section 15 converts the power supplied from battery section 11 or AC adapter section 12 into power suitable for each component, and supplies the power.

AC adapter section 12 can be connected to power plug 17, and when power plug 17 is connected with the AC power source, AC adapter section 12 performs AC-DC conversion and supplies the power to power source control section 14.

Battery section 11 is a rechargeable power source, and supplies the power charged therein to power source control section 14 when no power is supplied to AC adapter section 12. When the power of battery section 11 is exhausted, power is supplied to battery section 11 through power source control section 14 and AC adapter section 12 connected with the AC power source, so as to charge battery section 11.

AC adapter connection detecting section 13 monitors whether power is supplied to AC adapter section 12 from the AC power source, and transmits the resulting power connection determination signal to power source control section 14. The power connection determination signal specifically refers to an output signal which differs depending on whether power is supplied from AC power source or not, and thus allows for determination whether the apparatus is electrically connected with the AC power source or not.

Based on the power connection determination signal from AC adapter connection detecting section 13, power source control section 14 controls power supplying section 15 to transmit the power from AC adapter section 12, or the power from battery section 11, to each component.

Battery section 11 and AC adapter section 12 may also be connectable to ultrasonic diagnostic apparatus main body 00, rather than being provided inside ultrasonic diagnostic apparatus main body 00.

Ultrasonic probe 01 includes an oscillator. Ultrasonic probe 01 converts an electric signal received from ultrasonic transmission section 02 into ultrasonic waves, and transmits the ultrasonic waves emitted from the oscillator toward a subject, with ultrasonic probe 01 brought into contact with the surface of the subject. In addition, ultrasonic probe 01 receives ultrasonic waves reflected by the subject, and converts the reflected ultrasonic waves into corresponding received electric signals by the oscillator, and supplies the received electric signals to ultrasonic reception section 04.

Ultrasonic transmission section 02 supplies a transmitted electric signal for transmitting ultrasonic waves to the oscillator in ultrasonic probe 01. The transmitted electric signal for transmitting ultrasonic waves to the subject from ultrasonic probe 01 is controlled by transmission control section 03. It is to be noted that ultrasonic transmission section 02 may also be provided in ultrasonic probe 01.

Ultrasonic reception section 04 performs analog-digital conversion, gain adjustment and/or the like on the received electric signal received from ultrasonic probe 01, to thereby generate and acquire a received signal. Alternatively, a configuration may be adopted in which the process of generating the received signal from the received electric signal is performed in ultrasonic probe 01, and the ultrasonic reception section 04 disposed in ultrasonic diagnostic apparatus main body 00 acquires the received signal.

Signal processing section 05 performs various kinds of digital signal processes such as log compression and edge enhancement on the received signal generated by ultrasonic reception section 04, and then outputs the signal to image generation section 06.

Image generation section 06 performs various kinds of image conversion on data outputted from signal processing section 05 to generate image data for displaying an image on display section 10.

System control section 07 connects with ultrasonic transmission section 02, transmission control section 03, ultrasonic reception section 04, signal processing section 05, image generation section 06, operation section 08, main body external input-output section 09, display section 10, and power supplying section 15, and performs a system control of each component or between the components.

Based on various kinds of operations performed by a user, operation section 08 outputs an operation signal to system control section 07. Operation section 08 is composed of, for example, a button, a trackball, a touch panel or the like.

Main body external input-output section 09 is used to connect to an external device or the like. Main body external input-output section 09 inputs and outputs an image signal for storing and reading out, to/from the external device, an image data generated by image generation section 06, and system control section 07 performs the input/output control.

Display section 10 displays the image data generated by image generation section 06. When operation section 08 is composed of a touch panel, display section 10 may be a display section with a touch panel.

Figure 2:
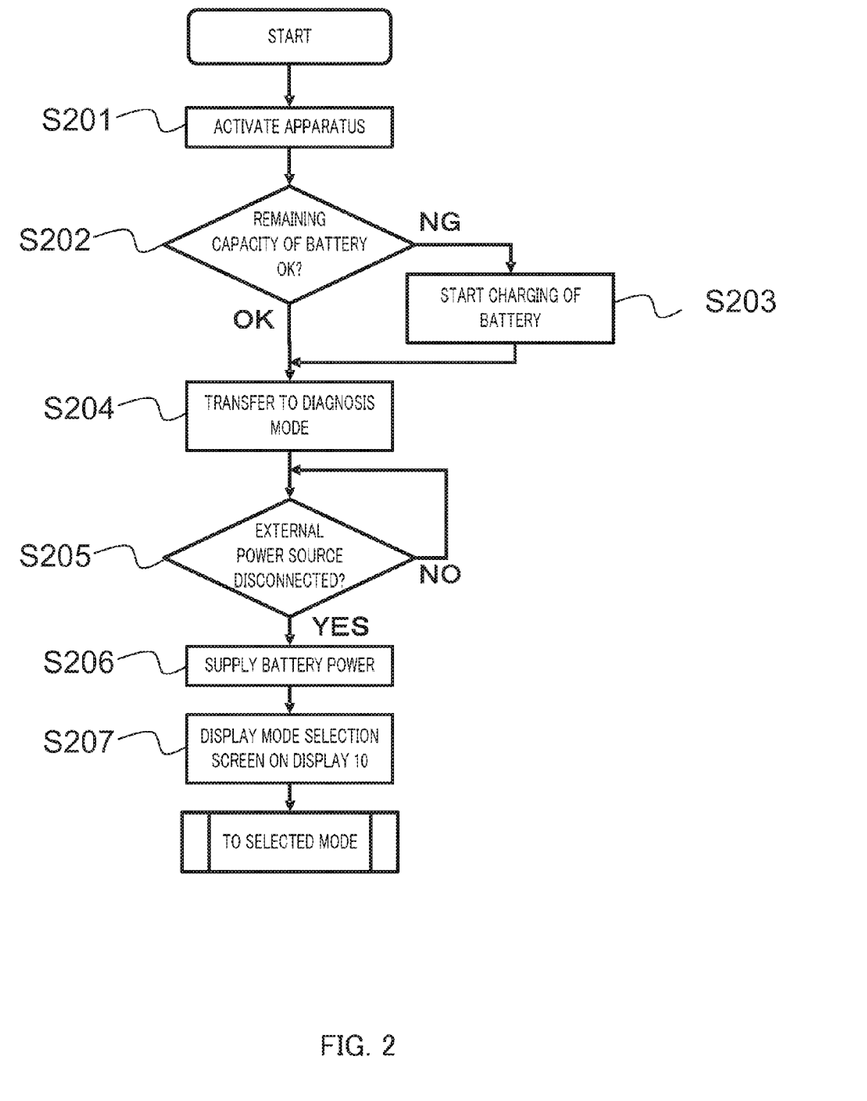
FIG. 2 is a flowchart of Embodiment 1 of the present invention.

Next, the operation of the ultrasonic diagnostic apparatus according to Embodiment 1 will be described with reference to FIG. 2. FIG. 2 is a flowchart illustrating an operation of ultrasonic diagnostic apparatus main body 00 of Embodiment 1.

In ultrasonic diagnostic apparatus main body 00, when power button 16 is pressed down, power source control section 14 detects the power connection determination signal transmitted from AC adapter connection detecting section 13, and determines whether AC adapter section 12 is electrically connected with the AC power source. In Embodiment 1 of the present invention, the flow will be described on the assumption that the AC adapter is connected with the AC power source when ultrasonic diagnostic apparatus main body 00 is activated.

At step S201, when power button 16 is pressed down, ultrasonic diagnostic apparatus main body 00 causes power source control section 14 to supply power from power supplying section 15 to each component, and system control section 07 is activated. Then initial setting such as the register setting of transmission control section 03, ultrasonic reception section 04, signal processing section 05, and image generation section 06 is performed.

Next, at step S202, power source control section 14 confirms the remaining capacity of battery section 11, and when the remaining capacity of the of battery is equal to or lower than a predetermined level, the processing is transferred to step S203, and when the remaining capacity of the battery is higher than the predetermined level, the processing is transferred to step S204.

At step S203, power source control section 14 controls power supplying section 15 to convert the power outputted from AC adapter section 12 into power suitable for battery section 11, and power supplying section 15 supplies the power thus converted to battery section 11, so as to start charging of the battery.

At step S204, ultrasonic diagnostic apparatus main body 00 changes to diagnosis mode. The diagnosis mode is a state where the display displays an actual ultrasonic diagnosis image, and the transmitted electric signal for transmitting ultrasonic waves is being supplied from ultrasonic transmission section 02 to the oscillator in ultrasonic probe 01.

The user performs diagnosis and inspection in the diagnosis mode of ultrasonic diagnostic apparatus main body 00.

At step S205, when AC adapter connection detecting section 13 detects that the power supplied from the AC power source is cut off, the processing is transferred to step S206. The power supplied from the AC power source is cut off when the user moves ultrasonic diagnostic apparatus main body 00 to a place distant from the AC power source; when power plug 17 has mistakenly fallen off from the AC power source, when the power of the AC power source is not supplied to the AC adapter due to power outage; and the like.

At step S206, AC adapter connection detecting section 13 outputs, to power source control section 14, a power connection determination signal indicating that the AC power source is disconnected. Further, when the power connection determination signal is received, power source control section 14 switches the power supply to the power supply from battery section 11. Thus, even when the power supplied from the AC power source is cut off, the power supplied to ultrasonic diagnostic apparatus main body 00 is not cut off, and ultrasonic diagnostic apparatus main body 00 can operate without being interrupted.

Figure 3:
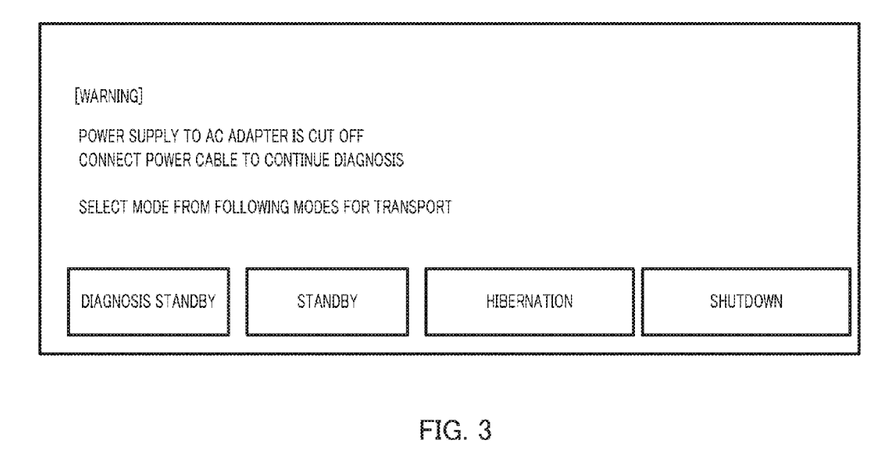
FIG. 3 illustrates a mode selection display screen according to Embodiment 1 of the present invention.

Next, at step S207, system control section 07 displays on display section 10 a screen for selecting modes. FIG. 3 illustrates an exemplary screen displayed on display section 10 at this step. Here, the screen requests the user to select any of four modes "diagnosis standby," "standby," "hibernation," and "shutdown." The user selects a mode using operation section 08. When the input from operation section 08 is received, ultrasonic diagnostic apparatus main body 00 transfers to the processing set in advance for each mode. The processing for each mode will be described below with reference to FIGS. 5 to 7.

Figure 5:
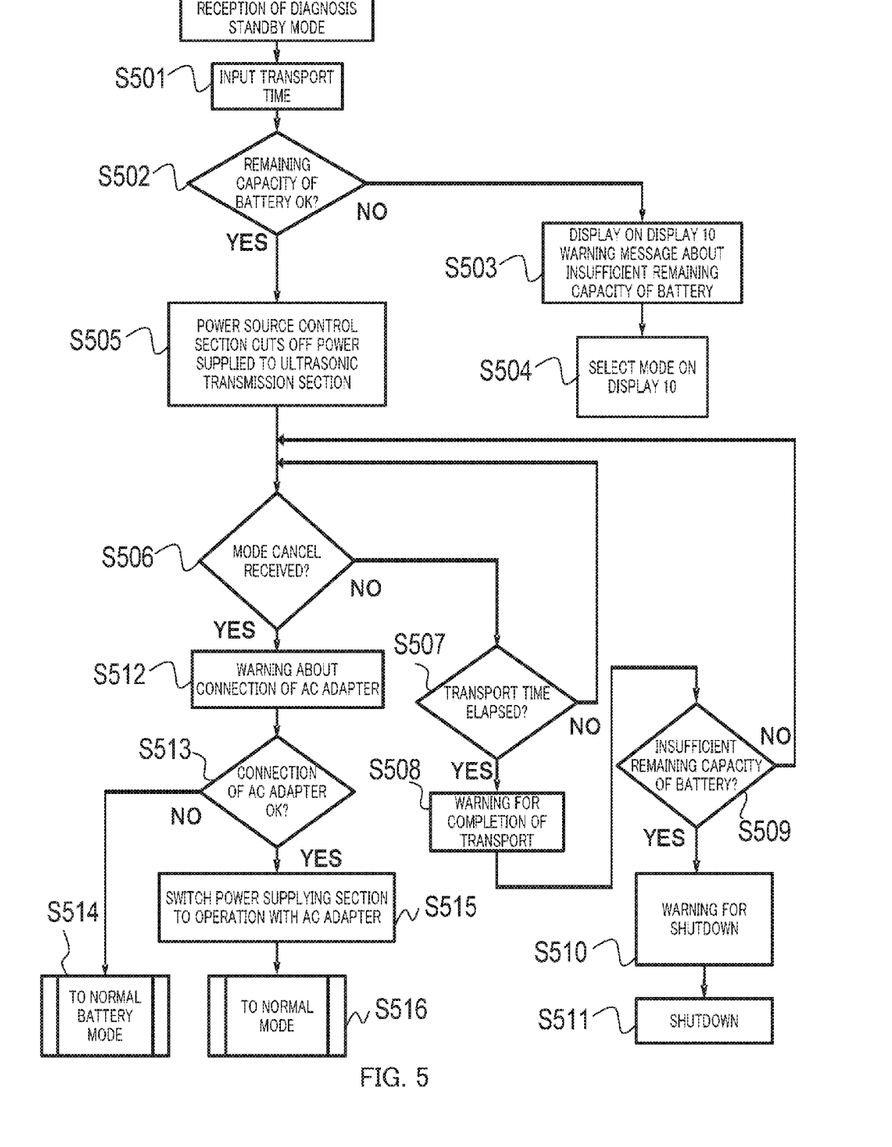
FIG. 5 is a flowchart illustrating a diagnosis standby mode according to Embodiment 1 of the present invention.

Next, with reference to FIG. 5, the following describes the processing which is carried out when the diagnosis standby mode is selected from among the modes displayed at step S207.

FIG. 5 illustrates the processing which is carried out when the user has selected the diagnosis standby.

The diagnosis standby mode is designed for the case where, for example, the user wants to move the ultrasonic diagnostic apparatus without completely turning off the power so as not to change the setting and the like, in other words, the case where the ultrasonic diagnosis is not performed. In the diagnosis standby mode, the power supplied to ultrasonic transmission section 02 is cut off while maintaining the power supplied to system control section 07, and the transmitted electric signal is not supplied to ultrasonic probe 01.

When a signal corresponding to selection of the diagnosis standby mode is received, system control section 07 transfers to the flow illustrated in FIG. 5.

Figure 4:
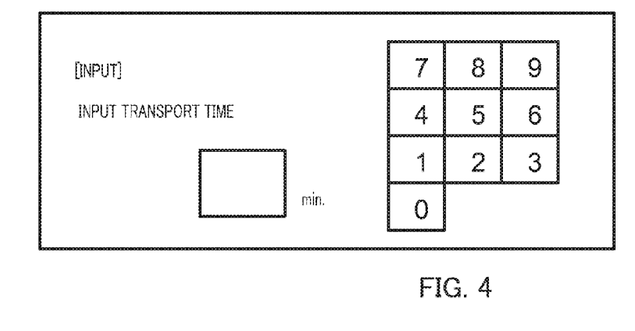
FIG. 4 illustrates a screen for inputting a transport time according to Embodiment 1 of the present invention.

First, at step S501, system control section 07 displays a screen that urges the user to input the period for which the user wants to continue the diagnosis standby mode, and receives an input of the period. The period for which the user wants to continue the diagnosis standby mode is, for example, transport time. FIG. 4 is an exemplary screen displayed on display section 10 at step S501. The user inputs an approximate transport time from operation section 08.

When the transport time is received, at step S502, system control section 07 compares the residual quantity in battery section 11 at this point of time with the power to be consumed for the transport time, and when the remaining capacity of the battery is insufficient, the processing is transferred to step S503, and when the remaining capacity of the battery is sufficient, the processing is transferred to step S505.

Specifically, the comparison between the remaining capacity of the battery and the power consumed for the transport time is carried out such that system control section 07 computes, based on the time period received at step S501, the power consumption of ultrasonic diagnostic apparatus main body 00 required for continuing the diagnosis standby mode for the time period, and compares the value of the power consumption thus computed with the value of the residual quantity in battery section 11. The power consumption required for continuing the diagnosis standby mode is the power consumed when the power supplied to transmission control section 03 of ultrasonic diagnostic apparatus main body 00 is cut off. When the power consumption thus computed is greater than the residual quantity in battery section 11, the remaining capacity of the battery is determined to be insufficient, and when the computed power consumption is smaller than the residual quantity in battery section 11, the remaining capacity of the battery is determined to be sufficient.

When the processing is transferred from step S502 to step S503, system control section 07 warns, on display section 10, that the remaining capacity of the battery is insufficient, at step S503. Further, at step S504, system control section 07 displays on display section 10 a screen that urges the user to select a mode other than the diagnosis standby mode. Here, when selection of a mode other than the diagnosis standby mode is received, the processing is transferred to the processing of the selected mode. A screen that urges the user to connect power plug 17 to the AC power source may also be displayed on display section 10.

When the processing is transferred from step S502 to step S505, at step S505, power source control section 14 cuts off the power supplied from power supplying section 15 to ultrasonic transmission section 02 so that ultrasonic transmission section 02 generates no transmitted electric signal. At this time, the power supplied to system control section 07, power supplying section 15, main body external input-output section 09, and power button 16 is not cut off, and transmission control section 03, ultrasonic reception section 04, signal processing section 05, image generation section 06, operation section 08, and AC adapter connection detecting section 13 are each set to a power saving mode in which the power supply amount is reduced, with the luminance of display section 10 decreased. Here, it suffices that the diagnosis standby mode is a mode in which at least the power supplied to ultrasonic transmission section 02 is cut off and the power supplied to system control section 07 is not cut off, and the amount of power of the other components may be appropriately set.

Next, at step S506, when system control section 07 does not receive a signal indicating that the diagnosis standby mode signal is canceled, the processing is transferred to step S507, and when system control section 07 receives the signal indicating that the diagnosis standby mode is canceled, the processing is transferred to step S512. Regarding the signal indicating that the diagnosis standby mode is canceled, for example, the apparatus can recognize that the signal indicating that the diagnosis standby mode is canceled is received when a signal indicating that power button 16 is pressed down is received in the diagnosis standby mode.

When the processing is transferred from step S506 to step S507, system control section 07 compares, at step S507, the time period received at step S501 with the period of the time elapsed from when the time period is received. When the elapsed time exceeds the received time period, the processing is transferred to step S508, and when the elapsed time does not exceed the received time period, the processing is returned to step S506.

At step S508, system control section 07 displays on display section 10 a warning message that urges the user to complete the transportation. An alarm may also be issued to warn the user.

Further, at step S509, power source control section 14 confirms the remaining capacity of the battery in battery section 11, and when the remaining capacity of the battery is equal to or lower than a predetermined level, the processing is transferred to step S510, and when the remaining capacity of the battery is higher than the predetermined level, the processing is transferred to step S506. It is to be noted that, when the remaining capacity of the battery is higher than the predetermined level and the processing is transferred to step S506, the succeeding steps S507 and S508 may be omitted.

When the processing is transferred from step S509 to step S510, system control section 07 displays on display section 10 a warning message indicating that the system of ultrasonic diagnostic apparatus main body 00 will be shutdown at step S510, and, at step S511, system control section 07 stores the current system setting of ultrasonic diagnostic apparatus main body 00, and then shuts down the system so as to safely stop ultrasonic diagnostic apparatus main body 00. Here, the system setting is the setting of image data, patient information, system control section 07, or the like.

When the processing is transferred from step S506 to step S512, at step S512, system control section 07 displays on display section 10 a warning message that urges connection to the AC power source.

Next, at step S513, when power source control section 14 recognizes that the apparatus is not electrically connected with the AC power source on the basis of on the power connection determination signal received from AC adapter connection detecting section 13, the processing is transferred to step S514, and when power source control section 14 recognizes that the apparatus is electrically connected with the AC power source, the processing is transferred to step S515.

When the processing is transferred from step S513 to step S514, at step S514, power source control section 14 cancels the diagnosis standby mode while maintaining the power supply from battery section 11. Specifically, disconnection of the power source relating to the ultrasonic transmission is canceled, and power is supplied to transmission control section 03 to establish a state where ultrasonic waves are transmitted from ultrasonic probe 01.

When the processing is transferred from step S513 to step S515, power source control section 14 switches the power supplied to power supplying section 15 to the power supplied from the power AC adapter section 12, at step S515.

Next, at step S516, the diagnosis standby mode is canceled. Specifically, disconnection of the power source relating to the ultrasonic transmission is canceled, and power is supplied to transmission control section 03 so as to establish a state where ultrasonic waves can be transmitted from ultrasonic probe 01.

Figure 6:
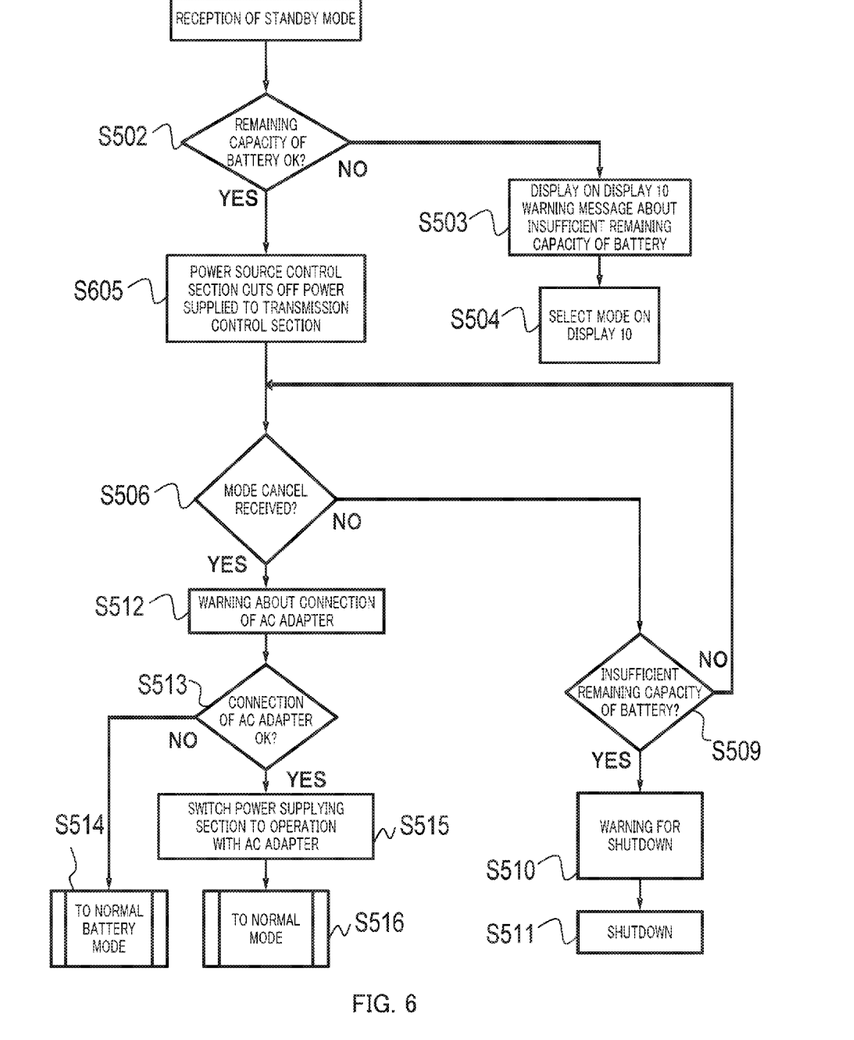
FIG. 6 is a flowchart illustrating a standby mode according to Embodiment 1 of the present invention.

Next, with reference to FIG. 6, the following describes a flow of processing which is performed when the standby mode is selected from among the modes displayed at step S207.

FIG. 6 illustrates the flow of the processing which is performed when the user has selected "standby."

Similarly to the diagnosis standby mode, the standby mode is designed for the case where, for example, the user wants to move the ultrasonic diagnostic apparatus without completely turning off the power so as not to change the setting, in other words, the case where ultrasonic diagnosis is not performed. The power consumption amount of the diagnosis standby mode is reduced in comparison with the case of the diagnosis standby mode. Although transition to a normal diagnosis mode takes more time in the standby mode in comparison with the case of the diagnosis standby mode, the standby mode can advantageously reduce the power consumption amount and can deal with long distance transportation. The standby mode is a power saving mode in which the amount of power supplied to system control section 07 is reduced as much as possible while the power supplied to the memory is maintained at the same level as in the normal operation so as to hold the setting, and the power supplied to transmission control section 03 is cut off so as not to supply transmitted electric signal to ultrasonic probe 01.

When system control section 07 receives a signal indicating that the standby mode is selected, the processing is transferred to the flow illustrated in FIG. 6. The same flow as those in the diagnosis standby mode illustrated in FIG. 5 will be denoted by the same reference numeral, and the description thereof will be omitted.

The standby mode differs from the diagnosis standby mode in that, when system control section 07 receives the signal indicating that the standby mode is selected, the processing of step S502 is performed while omitting step S501, and further, when system control section 07 does not receive a signal indicating that the diagnosis standby mode is cancelled at step S506, the processing is transferred to step S509 while omitting step S507 and step S508. In addition, the processing of step S605 is executed instead of the processing of step S505.

When the remaining capacity of the battery is determined to be sufficient at step S502, the processing is transferred to step S605, and at step S605, power source control section 14 cuts off power supplied from power supplying section 15 to ultrasonic transmission section 02, transmission control section 03, ultrasonic reception section 04, signal processing section 05, image generation section 06, operation section 08, main body external input-output section 09, display section 10, and AC adapter connection detecting section 13. At this time, the power supplied to power button 16 is maintained, and system control section 07 reduces the amount of power supply so as to establish a power saving mode in which only the memory in system control section 07 is energized. Here, it suffices that the standby mode is a mode in which at least the power supplied to transmission control section 03 and ultrasonic transmission section 02 is cut off and the amount of the power supplied to system control section 07 is reduced while the power supplied to the memory is maintained at the same level as in the normal operation so as to hold the setting, and the amount of power of the other components may be appropriately set.

Figure 7:
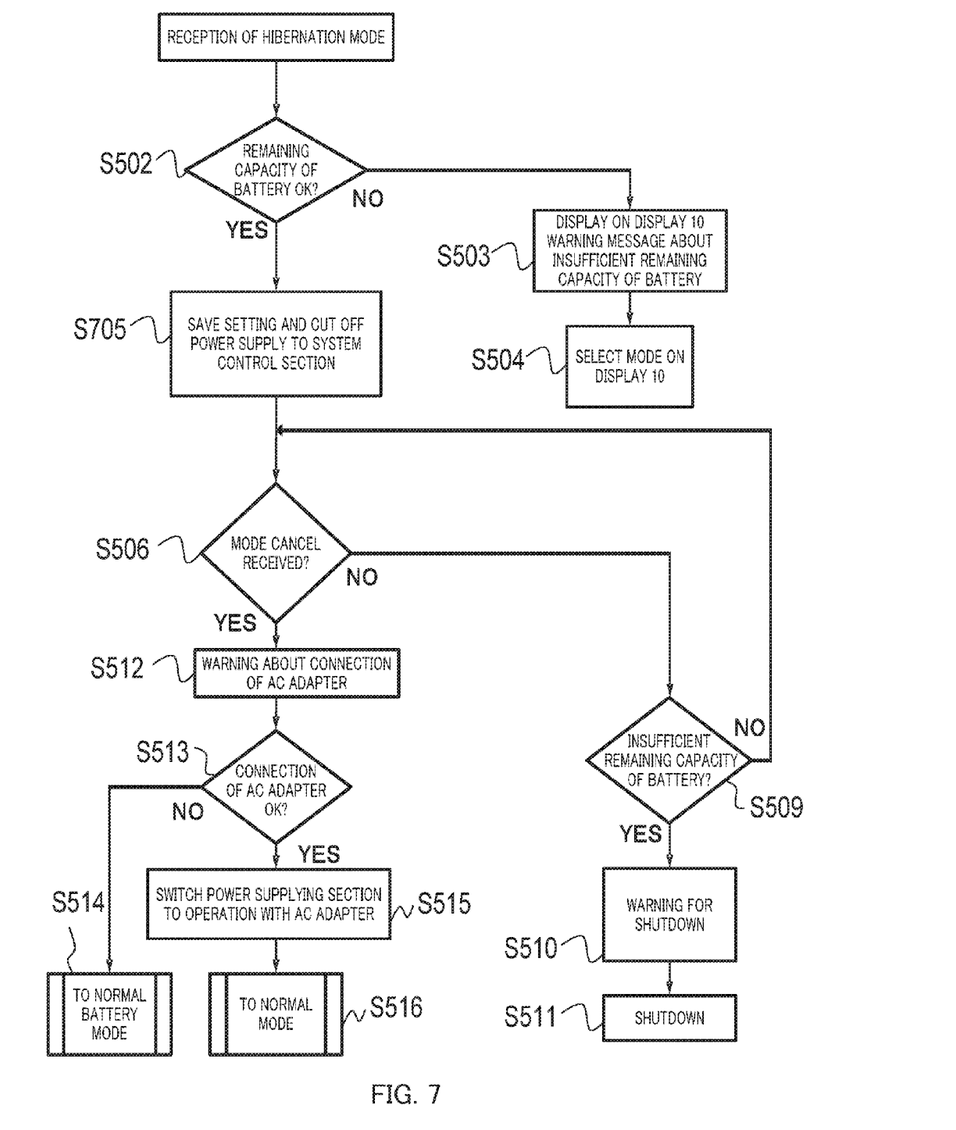
FIG. 7 is a flowchart illustrating a hibernation mode according to Embodiment 1 of the present invention.

Next, with reference to FIG. 7, the following describes a flow of processing which is performed when a hibernation mode is selected from among the modes displayed at step S207.

FIG. 7 illustrates the flow of the processing when the user has selected the hibernation.

The hibernation mode is designed for the case where the user wants to move the ultrasonic diagnostic apparatus with the power source turned off, in other words the case where the ultrasonic diagnosis is not performed, and the hibernation mode is a mode in which the setting of system control section 07 and the like are stored so that the diagnosis mode is activated with the setting stored in advance without resetting after the apparatus is moved. The hibernation mode is a mode in which the power consumption amount is further reduced in comparison with the standby mode. In the case where the power supplied to system control section 07 is cut off after the setting of system control section 07 is stored and then the mode is again transferred to the diagnosis mode, the setting stored in advance is used, and therefore, the time it takes before system control section 07 is again activated can be shortened in comparison with typical shutdown.

When system control section 07 receives a signal indicating that the hibernation mode is selected, the processing is transferred to the flow illustrated in FIG. 7. The same flow as that in the diagnosis standby mode illustrated in FIG. 5 will be denoted by the same reference numeral, and the description thereof will be omitted.

The hibernation mode differs from the diagnosis standby mode in that, when system control section 07 receives the signal indicating that the hibernation mode is selected, the processing of step S502 is performed while omitting step S501, and when system control section 07 does not receive a signal indicating that the diagnosis standby mode is canceled at step S506, the processing is transferred to step S509 while omitting step S507 and step S508. In addition, the processing of step S705 is executed instead of the processing of step S505.

When the remaining capacity of the battery is determined to be sufficient at step S502, the processing is transferred to step S705, and at step S705, the system setting stored in the memory in system control section 07 is stored in an external storage device (not illustrated) which is connected to system control section 07 in ultrasonic diagnostic apparatus main body 00, and power source control section 14 cuts off the power supplied from power supplying section 15 to ultrasonic transmission section 02, transmission control section 03, ultrasonic reception section 04, signal processing section 05, image generation section 06, operation section 08, main body external input-output section 09, display section 10, and AC adapter connection detecting section 13. Regarding the power supplied to system control section 07, the power is cut off except for the power required to cancel the hibernation mode, after the system setting has been stored. The power supplied to power button 16 is not cut off.

Next, when "shutdown" is selected from among the modes displayed at step S207, system control section 07 shuts down ultrasonic diagnostic apparatus main body 00.

It is to be noted that ultrasonic diagnostic apparatus main body 00 may be a hand-carry type, or a cart type mounted on a cart which can be moved by pushing.

The processing of each mode is merely an example, and it suffices that the power to be supplied to the components is set in advance so as to establish predetermined modes.

Embodiment 2

Figure 8:
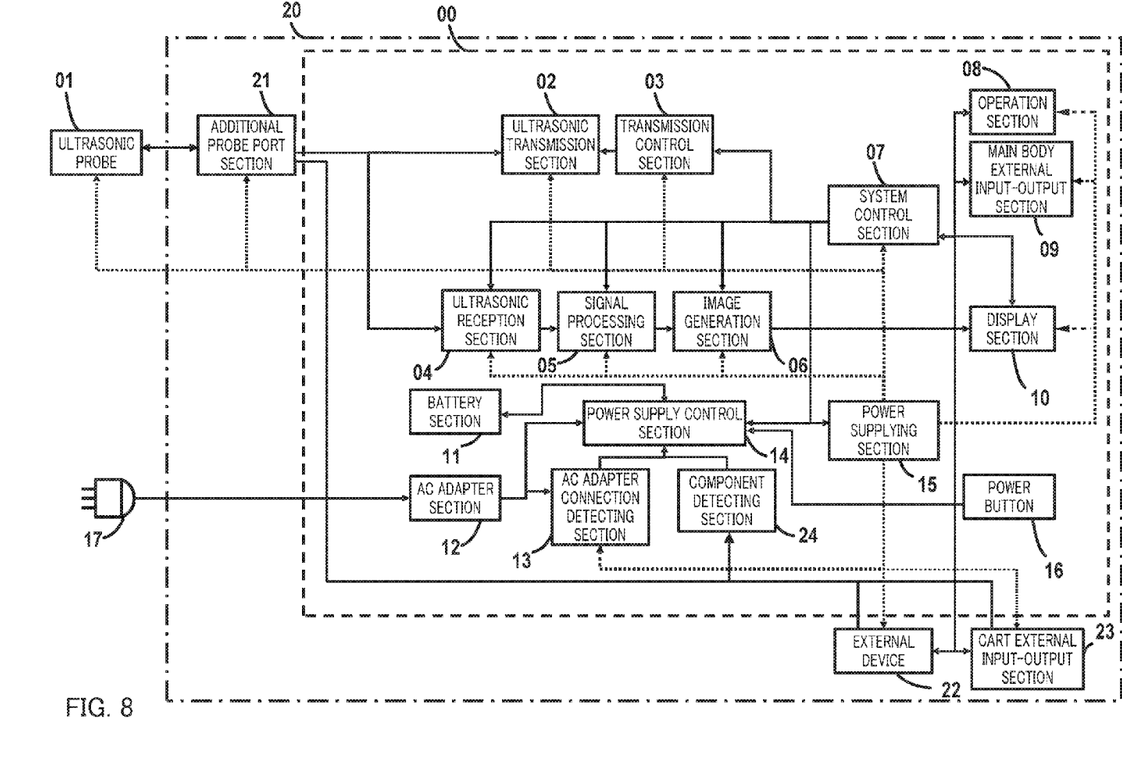
FIG. 8 illustrates a configuration of an ultrasonic diagnostic apparatus according to Embodiment 2 of the present invention.

Cart type ultrasonic diagnostic apparatus 20 having a configuration illustrated in FIG. 8 is, for example, one in which an ultrasonic diagnostic apparatus is provided on a cart with wheels and the like which allow slide movement. Cart type ultrasonic diagnostic apparatus 20 includes ultrasonic diagnostic apparatus main body 00, additional probe port section 21, external device 22, and cart external input-output section 23. Ultrasonic diagnostic apparatus main body 00 of Embodiment 2 differs from that of Embodiment 1 in that the former includes component detecting section 24. The configurations similar to those in Embodiment 1 will be denoted by the same reference numerals, and the description thereof will be omitted.

Ultrasonic diagnostic apparatus main body 00 includes ultrasonic transmission section 02, transmission control section 03, ultrasonic reception section 04, signal processing section 05, image generation section 06, system control section 07, operation section 08, main body external input-output section 09, display section 10, battery section 11, AC adapter section 12, AC adapter connection detecting section 13, power source control section 14, power supplying section 15, power button 16, and component detecting section 24. Ultrasonic diagnostic apparatus main body 00 is configured to be connectable to ultrasonic probe 01 and power plug 17.

Power plug 17 may be directly connected to ultrasonic diagnostic apparatus main body 00, or electrically connected to AC adapter section 12 of ultrasonic diagnostic apparatus main body 00 by providing cart type ultrasonic diagnostic apparatus 20 with a connection port for power plug 17.

Additional probe port section 21 is a connecting section to which multiple ultrasonic probes 01 can be connected, and different kinds of ultrasonic probes 01 may be connected thereto according to the intended use.

External device 22 is, for example, a storage device that stores therein a diagnostic image generated by image generation section 06. External device 22 is connected to main body external input-output section 09. External device 22 may also be a device that reads out data stored in a storage medium such as DVD.

Cart external input-output section 23 has a function similar to that of main body external input-output section 09, and is an expansion section intended for connection with various devices. Examples of cart external input-output section 23 include a USB port or HDMI (registered trademark) port, SD card insertion port, and LAN port.

Component detecting section 24 detects the connection state with each of additional probe port section 21, external device 22, and cart external input-output section 23, and outputs, to system control section 07, a component-connection determination signal which differs depending on the connection state. Here, as an example, detection of the connection state of additional probe port section 21 will be described in detail. Additional probe port section 21 outputs, to component detecting section 24, an individual connection determination signal whose voltage level changes when additional probe port section 21 is connected to a connecting section of ultrasonic probe 01. Component detecting section 24 can detect the connection state between additional probe port section 21 and ultrasonic probe 01 by detecting the individual connection determination signal. It is to be noted that, when component detecting section 24 according to the present embodiment is disposed in ultrasonic diagnostic apparatus main body 00 in Embodiment 1, component detecting section 24 can determine whether the device configuration is cart type ultrasonic diagnostic apparatus 20 or ultrasonic diagnostic apparatus main body 00 (including a hand-carry type).

It is to be noted that battery section 11 and AC adapter section 12 may be disposed inside or outside of the main body, and in addition, may be detachable and replaceable in anticipation for the case where battery section 11 and AC adapter section 12 are required to be replaced because of degradation and other causes.

Figure 9:
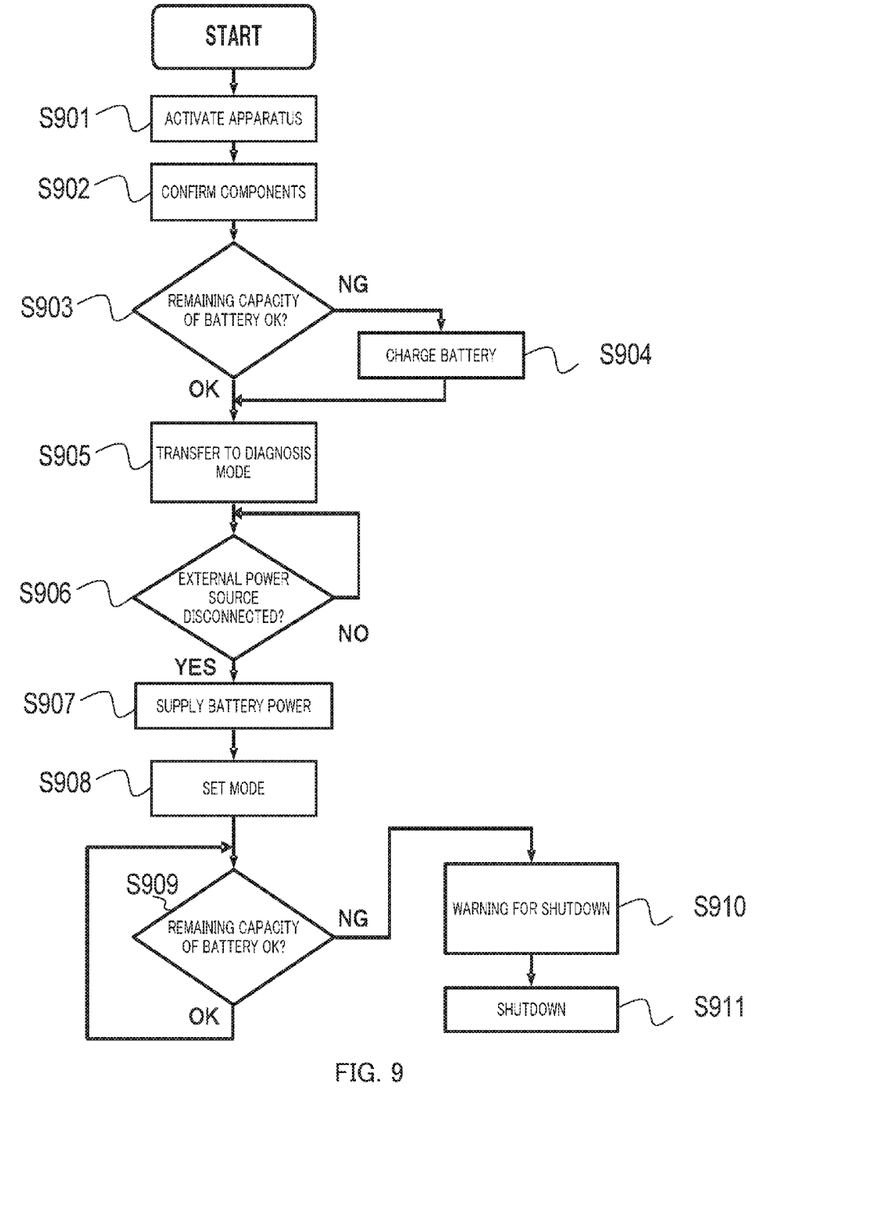
FIG. 9 is a flowchart of Embodiment 2 of the present invention.

Next, an operation of cart type ultrasonic diagnostic apparatus 20 according to Embodiment 2 will be described, with reference to FIG. 9. FIG. 9 is a flowchart illustrating the operation of ultrasonic diagnostic apparatus main body 00 of Embodiment 2.

In ultrasonic diagnostic apparatus main body 00, when power button 16 is pressed down, power source control section 14 detects the power connection determination signal transmitted from AC adapter connection detecting section 13, and determines whether AC adapter section 12 is electrically connected with the AC power source. In Embodiment 2 of the present invention, the flow will be described on the assumption that the AC adapter is connected with the AC power source when ultrasonic diagnostic apparatus main body 00 is activated.

At step S901, when power button 16 is pressed down, ultrasonic diagnostic apparatus main body 00 controls power source control section 14 to supply power from power supplying section 15 to each component, and system control section 07 is activated. Then initial setting such as the register setting of transmission control section 03 is performed.

Next, at step S902, component detecting section 24 detects the connection state with each of additional probe port section 21, external device 22, and cart external input-output section 23. To be more specific, the detection of the connection state of additional probe port section 21 means detecting the port in which the probe is connected, and the detection of the connection state of external device 22 means detecting whether external device 22 is connected with ultrasonic diagnostic apparatus main body 00, and the detection of the connection state of cart external input-output section 23 means detecting whether there is any device connected with cart external input-output section 23. Component detecting section 24 transmits a component-connection determination signal indicating the detected connection state to system control section 07.

Next, at step S903, power source control section 14 confirms the remaining capacity of the battery in battery section 11, and when the remaining capacity of the battery is equal to or lower than a predetermined level, the processing is transferred to step S904, and when the remaining capacity of the battery is higher than the predetermined level, the processing is transferred to step S905.

At step S904, power source control section 14 supplies the power outputted from AC adapter section 12 to battery section 11, and starts charging of the battery.

At step S905, ultrasonic diagnostic apparatus main body 00 changes to the diagnosis mode. The diagnosis mode is a state where the display displays an actual ultrasonic diagnosis image, and the transmitted electric signal for transmitting ultrasonic waves is supplied from ultrasonic transmission section 02 to the oscillator in ultrasonic probe 01.

The user performs diagnosis and inspection in the diagnosis mode of ultrasonic diagnostic apparatus main body 00.

At step S906, when AC adapter connection detecting section 13 detects that the power supplied from the AC power source is cut off, the processing is transferred to step S907. The power supplied from the AC power source is cut off when the user moves ultrasonic diagnostic apparatus main body 00 to a place distant from the AC power source; when power plug 17 has mistakenly fallen off from AC power source; when the power of the AC power source is not supplied to the AC adapter due to power outage; and the like.

At step S907, AC adapter connection detecting section 13 outputs the power connection determination signal indicating electrical disconnection of the AC power source to power source control section 14. Further, when the power connection determination signal is received, power source control section 14 switches the power supply to the power supply from battery section 11. Thus, even when the power supplied from the AC power source is cut off, the power supplied to ultrasonic diagnostic apparatus main body 00 is not cut off, and ultrasonic diagnostic apparatus main body 00 can operate without being interrupted.

Figure 10:
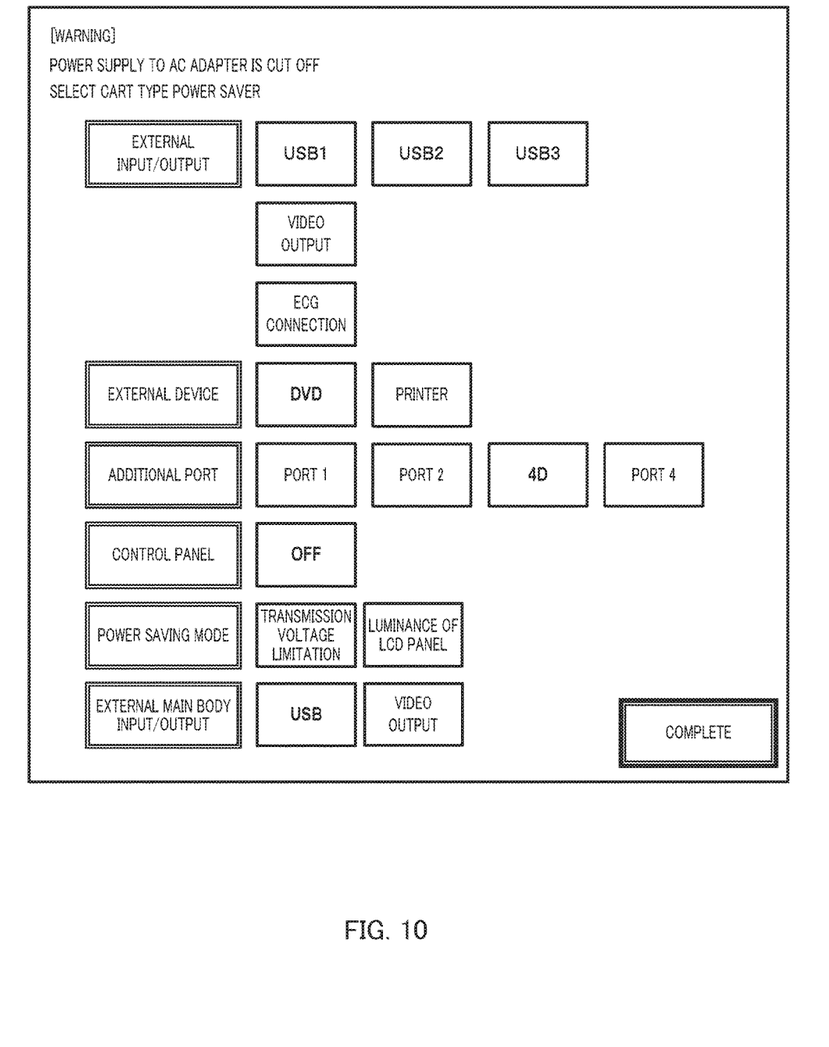
FIG. 10 illustrates a mode selection display screen according to Embodiment 2 of the present invention.

At step S908, system control section 07 displays on display section 10 a screen for selecting modes for adjusting power consumption. FIG. 10 illustrates an exemplary screen displayed on display section 10 at this time. Here, the screen requests the user to select any of: the components which are detected by component detecting section 24 at step S902 as being connected with cart external input-output section 23; external device 22; the port of additional probe port section 21 which is connected with ultrasonic diagnostic apparatus main body 00; the control panel, transmission control section 03, and the luminance of display section 10 included in ultrasonic diagnostic apparatus main body 00, and the components connected with main body external input-output section 09. From operation section 08, the user selects any of the components.

When an input from operation section 08 is received, ultrasonic diagnostic apparatus main body 00 reduces the power supplied to the selected component to a predetermined amount. The predetermined amount of power to be supplied may be set in advance or may be set by the user. Power source control section 14 controls the power to be supplied to the selected component so that the predetermined amount of power is supplied to the selected component. For example, in the case where the user wants to move cart type ultrasonic diagnostic apparatus 20 to some distant place, in other words, the case where ultrasonic diagnosis is not performed for a while, it is possible to cut off the power supplied to a part or all of the components connected with cart external input-output section 23, external device 22, additional probe port section 21, control panel, transmission control section 03, display section 10, and components connected with main body external input-output section 09.

Figure 11:
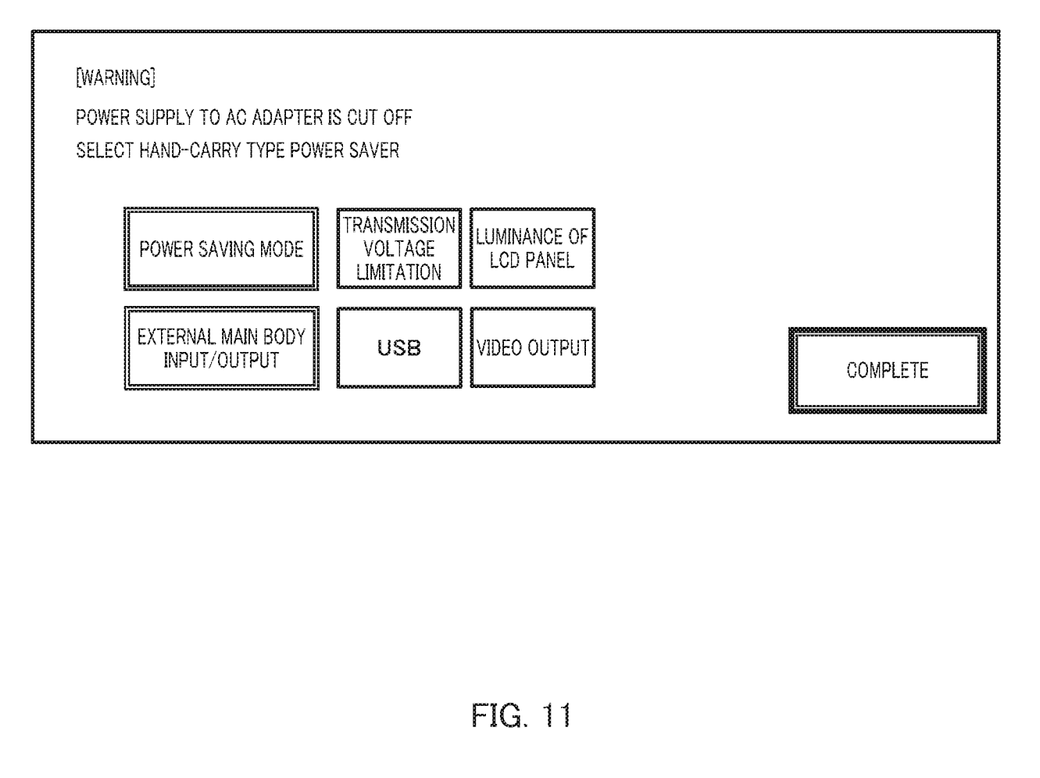
FIG. 11 illustrates a selection screen of a hand-carry type power saver according to Embodiment 2 of the present invention.

FIG. 11 illustrates another exemplary screen displayed on display section 10 at step S908. When it is determined, from the component-connection determination signal transmitted from component detecting section 24, that all of additional probe port section 21, external device 22 and cart external input-output section 23 are not connected with ultrasonic diagnostic apparatus main body 00, system control section 07 determines that the user is using the ultrasonic diagnostic apparatus main body 00 as a hand-carry type, not the configuration of cart type ultrasonic diagnostic apparatus 20, and as illustrated in FIG. 11, requests the user to select any of transmission control section 03 and the luminance of display section 10 included in ultrasonic diagnostic apparatus main body 00, and the components connected main body external input-output section 09.

That is, after the components connected with ultrasonic diagnostic apparatus main body 00 are determined at step S902, a screen is displayed at step S908 such that the user can select components whose power supply may be omitted.

From the selection screen displayed on display section 10 at step S908, the user cuts off the power supplied to the components for unnecessary functions according to the purpose, and thus the operating time by the battery is prolonged.

Next, at step S909, power source control section 14 confirms the remaining capacity of the battery in battery section 11, and when the remaining capacity of the battery is equal to or lower than a predetermined level, the processing is transferred to step S910.

At step S910, a warning message indicating that cart type ultrasonic diagnostic apparatus 20 is to be stopped is displayed on display section 10, and at step S911, system control section 07 stores the system setting and shuts down the apparatus such that cart type ultrasonic diagnostic apparatus 20 is safely stopped.

Also in Embodiment 2, as in Embodiment 1, it is also possible to request, at step S908, the user to make a selection from among modes set in advance based on the connection state of the components detected by component detecting section 24. This setting may be stored in ultrasonic diagnostic apparatus main body 00 in advance, or may be set by the user. For example, when component detecting section 24 determines that all of additional probe port section 21, external device 22 and cart external input-output section 23 are not connected with ultrasonic diagnostic apparatus main body 00, it is possible to request at step S908 the user to select the modes described with reference to FIG. 3. It is to be noted that the operations in respective modes are the same as the operations described with reference to FIGS. 5 to 7.

The present invention should not be limited to the above-mentioned embodiments, and the attachment/detachment detection, the power savers, the modes and the like may appropriately be changed. For example, the component whose connection is detected by component detecting section 24 may be, but not limited to, any of additional probe port section 21, external device 22 and cart external input-output section 23. Regarding the ultrasonic diagnostic apparatus main body 00 or cart type ultrasonic diagnostic apparatus 20, the embodiments of the present invention are applicable to all detachable components, component detecting section 24 can detect the connection of the components, and the power consumption amount can be set for each component.

INDUSTRIAL APPLICABILITY

The embodiments of the present invention may be utilized for an ultrasonic diagnostic apparatus which can be used while switching between an AC power source and a battery power source, and the like.

REFERENCE SIGNS LIST

00 Ultrasonic diagnostic apparatus main body
01 Ultrasonic probe
02 Ultrasonic transmission section
03 Transmission control section
04 Ultrasonic reception section
05 Signal processing section
06 Image generation section
07 System control section
08 Operation section
09 Main body external input-output section
10 Display section
11 Battery section
12 AC adapter section
13 AC adapter connection detecting section
14 Power supply control section
15 Power supplying section
16 Power button
17 Power plug
20 Cart type ultrasonic diagnostic apparatus
21 Additional probe port section
22 External device
23 Cart external input-output section
24 Component detecting section

The invention claimed is:

1. An ultrasonic diagnostic apparatus configured to be connectable to an ultrasonic probe, an AC power source and a battery, the battery being a rechargeable power source, the ultrasonic diagnostic apparatus comprising:
   a transmission control section configured to control generation of a transmitted electric signal to the ultrasonic probe for transmitting ultrasonic waves from the ultrasonic probe to a subject;
   an ultrasonic reception section configured to acquire a received signal from the ultrasonic probe based on reflected ultrasonic waves received by the ultrasonic probe;
   an AC adapter connection detector configured to detect whether the ultrasonic diagnostic apparatus is electrically connected with the AC power source; and
   a display, wherein,
   when the AC adapter connection detector detects that the AC power source is disconnected, power supply to the ultrasonic diagnostic apparatus is switched to power supply from the battery, and an operation screen is displayed on the display, the operation screen illustrating selectable modes for controlling an amount of power consumed by the ultrasonic diagnostic apparatus.

2. The ultrasonic diagnostic apparatus according to claim 1, wherein the operation screen is a mode selection screen from which whether to generate the transmitted electric signal or not is controlled.

3. The ultrasonic diagnostic apparatus according to claim 2, wherein the mode selection screen includes a mode for decreasing an amount of power supplied to the transmission control section.

4. The ultrasonic diagnostic apparatus according to claim 2, wherein the mode selection screen includes a mode for cutting off power supplied to the transmission control section.

5. The ultrasonic diagnostic apparatus according to claim 2 further comprising:
   a system control section connected with the transmission control section; and
   a storage connected with the system control section, wherein
   the mode selection screen includes a mode for cutting off power supplied to the system control section after storing a setting of the system control section in the storage.

6. The ultrasonic diagnostic apparatus according to claim 1 further comprising:
   an input-output port configured to transmit and receive a signal to and from an external device; and
   a component detector configured to detect a connection state between the input-output port and a device, wherein
   the operation screen is displayed based on the connection state.

7. The ultrasonic diagnostic apparatus according to claim 6, wherein
   the ultrasonic probe includes a plurality of ultrasonic probes,
   the input-output port is an additional probe port including a plurality of connectors that allow connection with the plurality of ultrasonic probes,
   the component detectors configured to detect a connection state between the additional probe port and the ultrasonic probe, and
   the operation screen is a screen from which the connector to which power is supplied is selected from among the connectors.

8. The ultrasonic diagnostic apparatus according to claim 1, wherein the operation screen is a screen from which whether to supply power to the display or not is selected.

9. The ultrasonic diagnostic apparatus according to claim 1, wherein
   the display is a touch-screen display, and
   the operation screen is a screen from which whether to supply power to the touch-screen display or not is selected.

10. The ultrasonic diagnostic apparatus according to claim 1 further comprising a system control section configured to receive an input about a certain period, compute a power consumption amount for the certain period, and compare the power consumption amount with an amount of power in the battery.

11. The ultrasonic diagnostic apparatus according to claim 1, wherein the operation screen presents a plurality of modes and requests a selection by a user of a mode for transport from the plurality of modes.

12. The ultrasonic diagnostic apparatus according to claim 11, wherein the plurality of modes includes a diagnosis standby mode, a standby mode, a hibernation mode, and a shut down mode, wherein
   in the diagnosis standby mode power supplied to an ultrasonic transmission section is cut off and power supplied to a system control section of the ultrasonic diagnostic apparatus is maintained,
   in the standby mode power supplied to the ultrasonic transmission section is cut off and power supplied to the system control section is reduced,
   in the hibernation mode a setting of the system control section is stored and power to the system is reduced, and
   in the shutdown mode the power to the ultrasonic diagnostic apparatus is cut off.

\* \* \* \* \*